US010517571B2

(12) United States Patent
Inui et al.

(10) Patent No.: US 10,517,571 B2
(45) Date of Patent: Dec. 31, 2019

(54) ULTRASOUND UNIT AND ULTRASOUND ENDOSCOPE

(71) Applicant: OLYMPUS CORPORATION, Tokyo (JP)

(72) Inventors: Satoshi Inui, Nagano (JP); Kazuya Matsumoto, Nagano (JP); Fukashi Yoshizawa, Ina (JP); Hiroshi Iwaisako, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 1406 days.

(21) Appl. No.: 14/145,138

(22) Filed: Dec. 31, 2013

(65) Prior Publication Data

US 2014/0114195 A1  Apr. 24, 2014

Related U.S. Application Data

(63) Continuation of application No. PCT/JP2012/065464, filed on Jun. 18, 2012.

(30) Foreign Application Priority Data

Jul. 4, 2011 (JP) .................................. 2011-148593

(51) Int. Cl.
*A61B 8/00* (2006.01)
*A61B 8/12* (2006.01)
(Continued)

(52) U.S. Cl.
CPC ................ *A61B 8/461* (2013.01); *A61B 8/12* (2013.01); *A61B 8/445* (2013.01); *A61B 8/4494* (2013.01)

(58) Field of Classification Search
None
See application file for complete search history.

(56) References Cited

U.S. PATENT DOCUMENTS

| 4,424,465 A * | 1/1984 | Ohigashi ............... B06B 1/0622 |
| | | 310/335 |
| 6,821,253 B2 * | 11/2004 | Wakabayashi ........ B06B 1/0622 |
| | | 310/336 |

(Continued)

FOREIGN PATENT DOCUMENTS

| CN | 101378605 A | 3/2009 |
| EP | 0 019 267 A1 | 11/1980 |

(Continued)

OTHER PUBLICATIONS

Extended Supplementary European Search Report dated Apr. 23, 2015 from related European Application No. 12 80 7399.6.

(Continued)

*Primary Examiner* — Thomas J Hong
*Assistant Examiner* — Shahdeep Mohammed
(74) *Attorney, Agent, or Firm* — Scully, Scott, Murphy & Presser, P.C.

(57) ABSTRACT

An ultrasound unit includes an ultrasound array that has a plurality of ultrasound elements, each of which has a first principal surface that is rectangular where a transmitting and receiving portion, a signal electrode terminal, and a ground electrode terminal are arranged in a longer side direction, longer sides of the ultrasound elements being coupled, one or more short-lines that are connected to a plurality of ground electrode terminals, a ground line that is connected to the short-line, and a plurality of signal lines, each of which is connected to one of the signal electrode terminals, and adjoining ultrasound elements of the ultrasound elements are coupled such that the signal electrode terminals are arranged alternately on opposite sides in the longer side direction of the transmitting and receiving portions that are rectangular.

11 Claims, 10 Drawing Sheets

(51) Int. Cl.
  *B06B 1/02* (2006.01)
  *B06B 1/06* (2006.01)

(56) References Cited

U.S. PATENT DOCUMENTS

| | | | |
|---|---|---|---|
| 8,047,995 | B2 | 11/2011 | Wakabayashi et al. |
| 2009/0058228 | A1* | 3/2009 | Wakabayashi ........ B06B 1/0292 310/334 |
| 2010/0179430 | A1 | 7/2010 | Sano et al. |
| 2010/0274138 | A1* | 10/2010 | Mizunuma ............ B06B 1/0629 600/459 |
| 2011/0071396 | A1 | 3/2011 | Sano et al. |

FOREIGN PATENT DOCUMENTS

| | | |
|---|---|---|
| EP | 1 897 498 A1 | 3/2008 |
| EP | 2 030 698 A1 | 3/2009 |
| EP | 2 130 495 A1 | 12/2009 |
| EP | 2 289 419 A1 | 3/2011 |
| JP | 52-011926 A | 1/1977 |
| JP | 55-103840 A | 8/1980 |
| JP | 62-192651 A | 8/1987 |
| JP | 63-260299 A | 10/1988 |
| JP | 64-027400 A | 1/1989 |
| JP | 2005-304692 A | 11/2005 |
| JP | 2009-055475 A | 3/2009 |
| JP | 4377787 B2 | 12/2009 |
| WO | WO 2008114582 A1 | 9/2008 |
| WO | WO 2009139400 A1 | 11/2009 |

OTHER PUBLICATIONS

Caliano, Giusuc et al., "Design, Fabrication and Characterization of a Capacitive Micromachined Ultrasonic Probe for Medical Imaging", IEEE Transactions on Ultrasonics, Ferroelectrics, and Frequency Control (Dec. 2005), vol. 52, No. 12, pp. 2259-2269.
English Abstract of JP 2006-087708, dated Apr. 6, 2006.
International Search Report dated Sep. 11, 2012 issued in PCT/JP2012/065464.

* cited by examiner

ULTRASOUND UNIT AND ULTRASOUND ENDOSCOPE

CROSS REFERENCE TO RELATED APPLICATION

This application is a continuation application of PCT/JP2012/065464 filed on Jun. 18, 2012 and claims benefit of Japanese Application No. 2011-148593 filed in Japan on Jul. 4, 2011, the entire contents of which are incorporated herein by this reference.

BACKGROUND OF THE INVENTION

1. Field of the Invention

The present invention relates to an ultrasound unit having an ultrasound element and an ultrasound endoscope including the ultrasound unit.

2. Description of the Related Art

An ultrasound endoscope can clearly visualize a wall of a digestive tract, a deep organ, or the like with good image quality free of influence of gas or a bone in a body. In an electron scanning type ultrasound endoscope, an ultrasound unit having an ultrasound array is disposed at a distal end portion. The ultrasound array is constructed by coupling longer sides of a plurality of ultrasound elements, each of which has a first principal surface that is elongated and rectangular. In each ultrasound element, a transmitting and receiving portion, a signal electrode terminal for transmitting and receiving a signal, and a ground electrode terminal at a ground potential are arranged in a longer side direction.

One signal line (coaxial cable core wire) is connected to the signal electrode terminal of each ultrasound element by, e.g., soldering, and one ground line (coaxial cable shielding wire) is connected to the ground electrode terminal.

A specification of Japanese Patent No. 4377787 discloses a transducer which connects an ultrasound array and coaxial cables by using a hollow cylindrical member having a relay electrode. In the transducer, electrode terminals of ultrasound elements and relay electrode terminals are connected with wires, and the coaxial cables are connected to the relay electrode terminals.

SUMMARY OF THE INVENTION

An ultrasound unit according to an embodiment of the present invention includes an ultrasound array that has a plurality of ultrasound elements, in each of which a transmitting and receiving portion including a signal electrode for transmitting and receiving ultrasound and a ground electrode, a signal electrode terminal connected to the signal electrode, and a ground electrode terminal connected to the ground electrode are disposed, longer sides of the plurality of ultrasound elements being coupled, one or more short-lines that are connected to a plurality of the ground electrode terminals, a ground line that is connected to the short-line, and a plurality of signal lines, each of which is connected to one of the signal electrode terminals, and adjoining ultrasound elements of the ultrasound elements are coupled such that the signal electrode terminals are arranged alternately on opposite sides in a longer side direction of the transmitting and receiving portions that are rectangular.

An ultrasound endoscope according to another embodiment includes an ultrasound unit which includes an ultrasound array that has a plurality of ultrasound elements, in each of which a transmitting and receiving portion including a signal electrode for transmitting and receiving ultrasound and a ground electrode, a signal electrode terminal connected to the signal electrode, and a ground electrode terminal connected to the ground electrode are disposed at a first principal surface, longer sides of the plurality of ultrasound elements being coupled, one short-line that is connected to a plurality of the ground electrode terminals, a ground line that is connected to the short-line, and a plurality of signal lines, each of which is connected to one of the signal electrode terminals, in which adjoining ultrasound elements of the ultrasound elements are coupled to bend in a convex shape or a radial shape in a coupling direction such that the signal electrode terminals are arranged alternately on opposite sides in a longer side direction of the transmitting and receiving portions that are rectangular, and in which the plurality of ground electrode terminals are laid out in a straight line shape.

DETAILED DESCRIPTION OF THE PREFERRED EMBODIMENTS

First Embodiment

An ultrasound unit (hereinafter referred to as a "US unit") 30 according to a first embodiment and an ultrasound endoscope (hereinafter referred to as a "US endoscope") 2 having the US unit 30 will be described below with reference to the drawings.

<Configuration of Ultrasound Endoscope>

Figure 1:
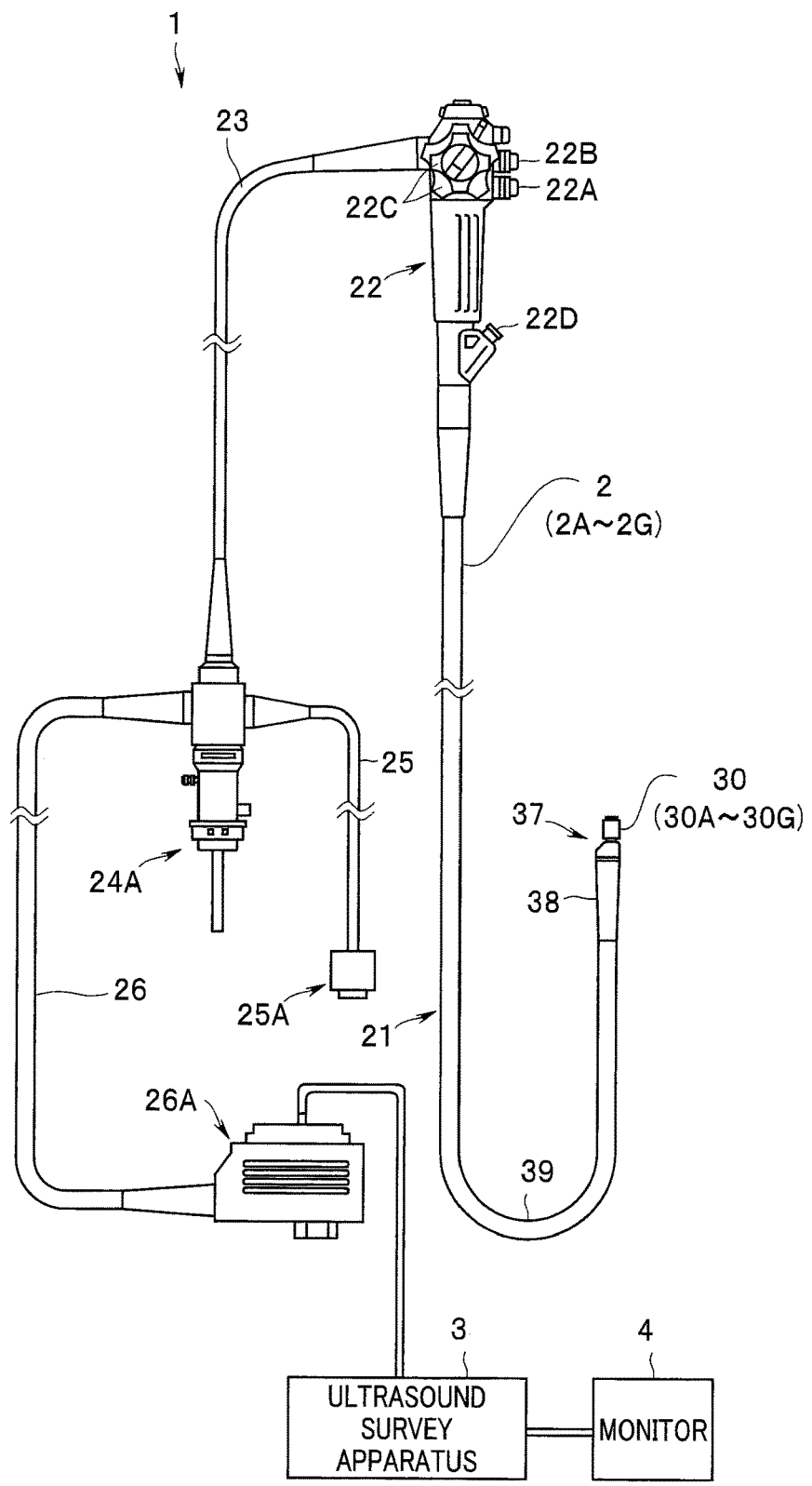
FIG. 1 is an external view for explaining an endoscope system including an ultrasound endoscope according to a first embodiment.

As shown in FIG. 1, the US endoscope 2 together with an ultrasound survey apparatus 3 and a monitor 4 constitutes an ultrasound endoscope system 1. The US endoscope 2 includes an elongated insertion portion 21 to be inserted into a body, an operation portion 22 which is placed at a proximal end of the insertion portion 21, and a universal cord 23 which extends from a side portion of the operation portion 22.

A connector 24A which is connected to a light source apparatus (not shown) is disposed at a proximal end portion of the universal cord 23. A cable 25 which is detachably connected to a camera control unit (not shown) via a connector 25A and a cable 26 which is detachably connected to the ultrasound survey apparatus 3 via a connector 26A extend from the connector 24A. The monitor 4 is connected to the ultrasound survey apparatus 3.

The insertion portion 21 is composed of a distal end rigid portion (hereinafter referred to as a "distal end portion") 37, a bending portion 38 located at a rear end of the distal end portion 37, and a thin, long, flexible tube portion 39 with flexibility located at a rear end of the bending portion 38 and leading to the operation portion 22, which are provided to be linked in order from a distal end side. The ultrasound unit 30 serving as an ultrasound transmitting and receiving portion is disposed on a distal end side of the distal end portion 37.

An angle knob 22A which bends and controls the bending portion 38 in a desired direction, an air/water feeding button 22B which performs air feeding and water feeding operation, a suction button 22C which performs suction operation, a treatment instrument insertion port 22D which serves as an inlet for a treatment instrument to be introduced into a body, and the like are disposed at the operation portion 22.

Figure 2:
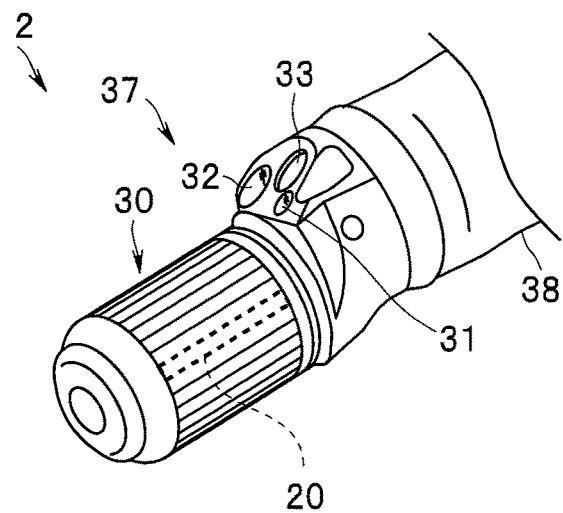
FIG. 2 is a perspective view for explaining a distal end portion of the ultrasound endoscope according to the first embodiment.

As shown in FIG. 2, a lens cover 31 for illumination which constitutes an illumination optical system, a lens cover 32 for observation of an observation optical system, a forceps port 33 which doubles as a suction port, and an air/water feeding nozzle (not shown) are disposed at the distal end portion 37 where the US unit 30 that transmits and receives ultrasound is provided.

Figure 3:
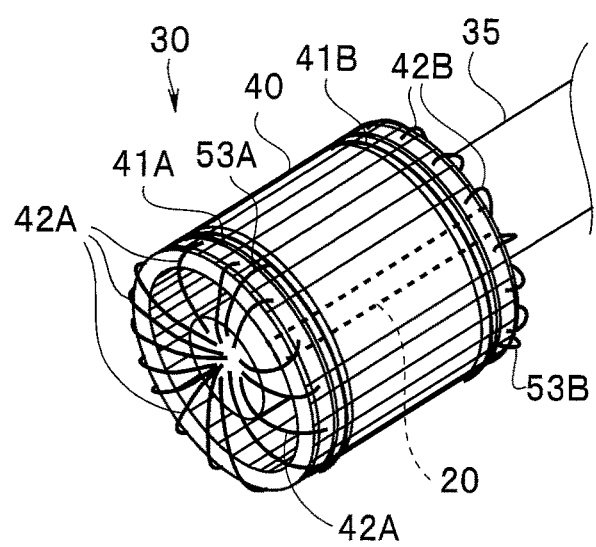
FIG. 3 is a perspective view for explaining a configuration of an ultrasound unit according to the first embodiment.

As shown in FIG. 3, the US unit 30 includes an ultrasound array (hereinafter referred to as a "US array") 40, short-lines 41A and 41B, ground lines 53A and 53B, and signal lines 42A and 42B. Note that, to refer to each of identical components, a reference numeral obtained by omitting an alphabetic character at an end of any one of reference characters denoting the identical components is used. For example, each of the short-lines 41A and 41B is referred to as the short-line 41. For example, the short-line 41A is the short-line 41 on a distal end side, and the short-line 41B is the short-line 41 on a proximal end side.

The US array 40 is a group of radial type transducers in which longer sides of a plurality of elongated US elements 20 are coupled, and the US elements 20 are arranged to bend in a hollow cylindrical shape. That is, in the US array 40, for example, 200 US elements 20 with shorter sides of not more than 0.1 mm are disposed at a side face of a hollow cylinder having a diameter of 2 mm.

Note that although the US array 40 is a group of radial type transducers, the US array 40 may be a group of convex type transducers which bends in a convex shape.

A plurality of signal lines 42 are each connected to a signal electrode terminal 52 of one US element 20. The short-line 41 is a short-line which connects ground electrode terminals 51 of the plurality of US elements 20 and is connected to the ground line 53.

The plurality of US elements 20 and a coaxial cable bundle 35 are connected via the short-lines 41, the ground lines 53, the signal lines 42, and a cable connection substrate portion (not shown). That is, the coaxial cable bundle 35 is made up of coaxial cables with core wires equal in number to the plurality of signal lines 42.

The coaxial cable bundle 35 is inserted through the distal end portion 37, the bending portion 38, the flexible tube portion 39, the operation portion 22, the universal cord 23, and the ultrasound cable 26 and is connected to the ultrasound survey apparatus 3 via the ultrasound connector 26A.

<Configuration of Ultrasound Array>

Figure 4:
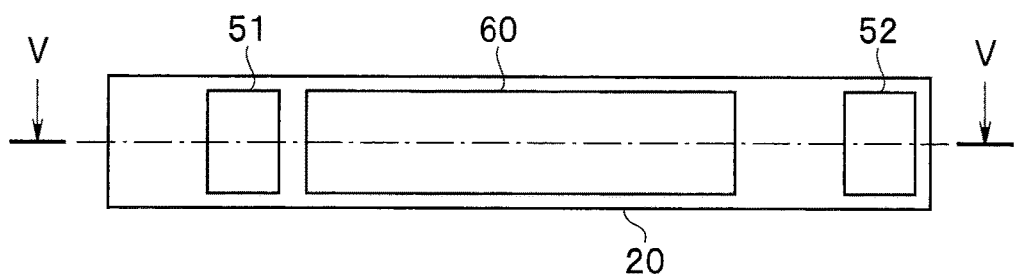
FIG. 4 is a top view of an ultrasound element of the ultrasound unit according to the first embodiment.
Figure 5:
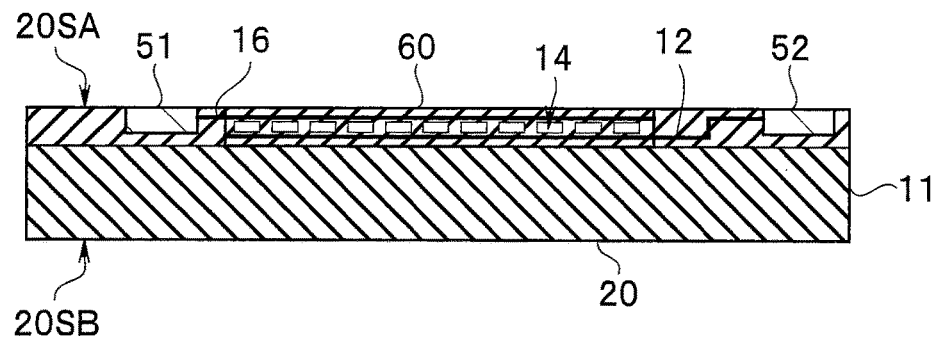
FIG. 5 is a cross-sectional view of the ultrasound element of the ultrasound unit according to the first embodiment, taken along line V-V in FIG. 4.

As shown in FIGS. 4 and 5, a transmitting and receiving portion 60, the signal electrode terminal 52, and the ground electrode terminal 51 are arranged in a longer side direction at a first principal surface 20SA that is rectangular of each US element 20. Note that the drawings are all schematic views for explanation and that ratios of thickness, size, and the like are different from actual ratios.

In the US element 20, the signal electrode terminal 52 and the ground electrode terminal 51 are arranged across the transmitting and receiving portion 60 from each other. A space where the ground electrode terminal 51 can be arranged is present between the transmitting and receiving portion 60 and the signal electrode terminal 52, and a space where the signal electrode terminal 52 can be arranged is present between the ground electrode terminal 51 and an end face. In other words, the transmitting and receiving portion 60, two signal electrode terminals 52, and two ground electrode terminals 51 can be arranged in the longer side direction at the first principal surface 20SA of the US element 20.

The signal electrode terminal 52 is connected to a lower electrode 12 which is a signal electrode of the transmitting and receiving portion 60. The ground electrode terminal 51 is connected to an upper electrode 16 which is a ground electrode of the transmitting and receiving portion 60.

The transmitting and receiving portion 60 generates ultrasound by a signal for driving applied between the lower electrode 12 and the upper electrode 16. The transmitting and receiving portion 60 also generates an electrical signal between the lower electrode 12 and the upper electrode 16 upon receipt of ultrasound.

<Configuration of Transmitting and Receiving Portion>

A configuration of the transmitting and receiving portion 60 will be described with reference to FIGS. 6 and 7.

Figure 6:
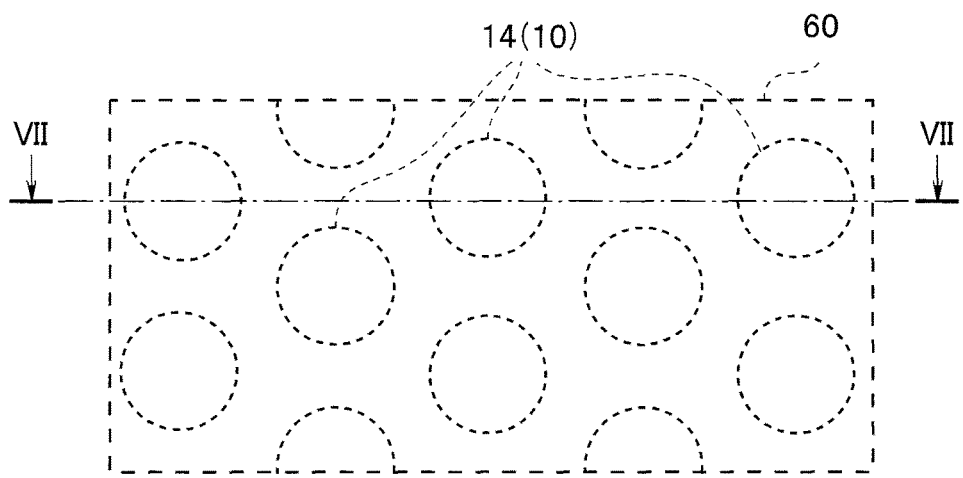
FIG. 6 is a top view of a transmitting and receiving portion of the ultrasound unit according to the first embodiment.

As shown in FIG. 6, a plurality of capacitance type ultrasound cells (hereinafter referred to as "US cells") 10 are arranged in a matrix at the transmitting and receiving portion 60 of the ultrasound unit 30. The US cells 10 may be arranged in a regular pattern, such as a grid pattern, a staggered pattern, or a triangular mesh pattern, or may be randomly arranged.

Figure 7:
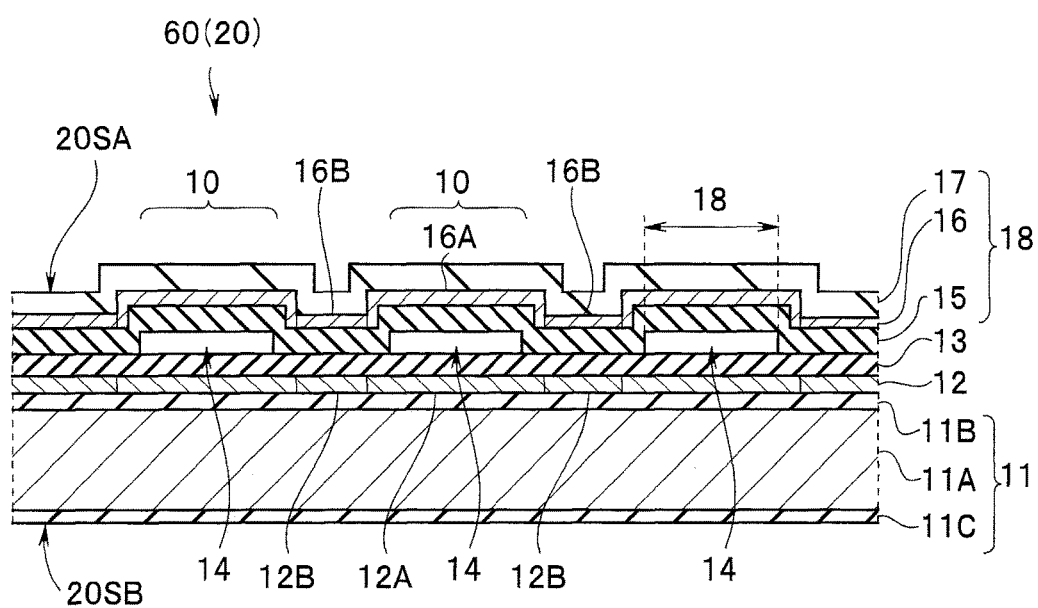
FIG. 7 is a cross-sectional view of the transmitting and receiving portion of the ultrasound unit according to the first embodiment, taken along line VII-VII in FIG. 6.

As shown in FIG. 7, the US cell 10 has, on a silicon substrate 11 as a base, the lower electrode 12 connected to the signal electrode terminal 52, a first insulating layer (lower insulating layer) 13, a second insulating layer (upper insulating layer) 15 in which a cavity 14 in a hollow cylindrical shape is formed, the upper electrode 16 connected to the ground electrode terminal 51, and a protective layer 17, which are stacked in order.

That is, each US cell 10 has a lower electrode portion 12A that is a circular signal electrode portion and a circular upper electrode portion 16A that is a ground electrode portion, which are arranged to face each other via the cavity 14. A plurality of lower electrode portions 12A constitute the lower electrode 12 serving as the signal electrode, and a plurality of upper electrode portions 16A constitute the upper electrode 16 serving as the ground electrode. That is, the lower electrode portions 12A of the plurality of US cells 10 arranged at the identical US element 20 are connected to one another, and the upper electrode portions 16A are also connected to one another.

The silicon substrate 11 is a substrate in which silicon thermal oxide films 11B and 11C are formed on surfaces of silicon 11A. The lower electrode 12 formed on one surface of the silicon substrate 11 is made of a conductive material, such as metal or silicon. A film of the conductive material is formed over the whole surface of the silicon substrate 11 by, e.g., sputtering. The lower electrode 12 is formed by partially removing the film through etching after forming a mask pattern through photolithography.

For example, the lower electrode 12 is made up of the circular lower electrode portions 12A and a wiring portion 12B which is provided to extend from an edge portion of the lower electrode 12. The lower electrode portion 12A is connected to the lower electrode portions of the other US cells of the identical US element 20 by the wiring portion 12B.

The first insulating layer 13 that is made of an insulating material, such as SiN, is formed by, e.g., CVD (chemical vapor deposition) so as to cover the lower electrode 12.

A sacrificial layer in a shape of the cavity 14 (a solid cylindrical shape) is formed by forming a film of a sacrificial layer material on the first insulating layer 13 and patterning the film.

Since a thickness of the sacrificial layer corresponds to a height of the cavity 14, the thickness is, for example, 0.05 to 0.3 μm, preferably 0.05 to 0.15 μm. For example, phosphorus glass (PSG: phosphorus-containing silicon oxide), silicon dioxide, polysilicon, metal, or the like is used as the sacrificial layer material.

The second insulating layer 15 is formed on an upper surface of the first insulating layer 13 where a sacrificial layer pattern is formed by, for example, the same method using the same material as the first insulating layer 13.

An opening portion (not shown) for admission of an etchant is formed at a predetermined position of the second insulating layer 15 to remove the sacrificial layer.

The cavity 14 is formed by etching the sacrificial layer. For example, if phosphorus glass is used for the sacrificial layer, and SiN is used for the first insulating layer 13 and the second insulating layer 15, a hydrofluoric acid solution (buffered HF solution) is used as the etchant.

The upper electrode 16 that is made up of the upper electrode portion 16A and a wiring portion 16B is formed in the same manner as the lower electrode 12. For example, the upper electrode portion 16A and the lower electrode portion 12A have substantially identical diameters as the cavity 14.

The cavity 14 is not limited to a solid cylindrical shape and may have, e.g., a polygonal column shape. If the cavity 14 has a polygonal column shape, shapes of the upper electrode portion 16A and the lower electrode portion 12A are preferably polygonal.

Finally, the protective layer 17 that covers the upper electrode 16 is formed. The protective layer 17 is an insulating layer which is formed by the same method using the same material as the second insulating layer 15. Note that the protective layer 17 may have a double-layered structure in which a skin film with biocompatibility of, e.g., polyparaxylylene is further formed on an insulating layer made of, e.g., SiN.

In the US cell 10 with the above-described structure shown in FIG. 7, the second insulating layer 15, the upper electrode 16, and the protective layer 17 in a region immediately above the cavity 14 constitute a membrane 18 serving as a vibration portion.

<Configurations of Ultrasound Array and Ultrasound Unit>

Figure 8:
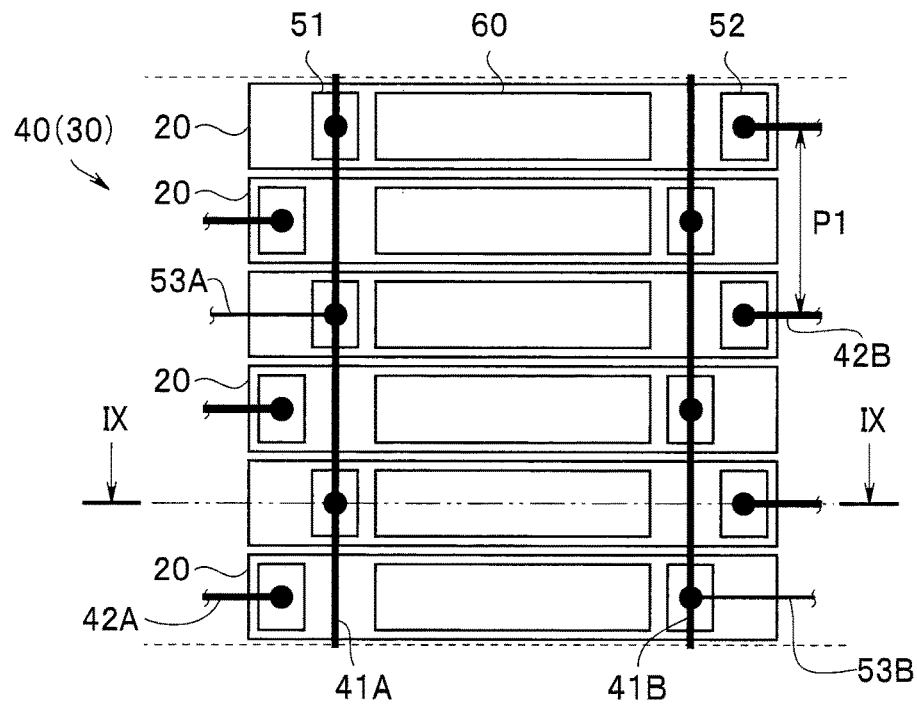
FIG. 8 is a plan developed view of an ultrasound array of the ultrasound unit according to the first embodiment.
Figure 9:
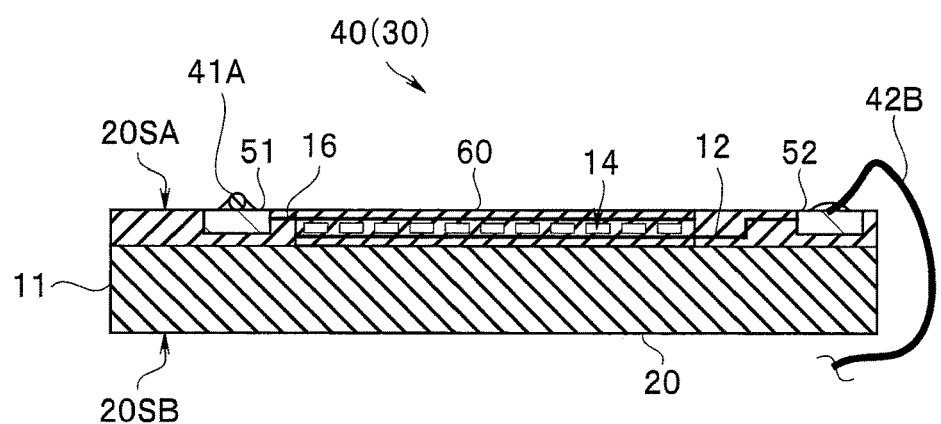
FIG. 9 is a cross-sectional view of the ultrasound array of the ultrasound unit according to the first embodiment, taken along line IX-IX in FIG. 8.

FIG. 8 is a plan developed view of the US unit 30, i.e., an explanatory view showing the plurality of US elements 20 laid out on a radial surface (a side face of a hollow cylinder) in a planar state. FIG. 9 is a cross-sectional view taken along line IX-IX in FIG. 8.

As has already been described, the longer sides of the plurality of US elements 20 of the US array 40 are coupled. As shown in FIG. 8, the plurality of US elements 20 with an identical configuration are coupled in a state where the US elements 20 are alternately rotated by 180° along the longer side direction such that the signal electrode terminal 52 of each US element 20 and the ground electrode terminal 51 of the adjoining US element 20 adjoin.

That is, the US array 40 is fabricated by linking the plurality of US elements 20 with an identical structure while changing disposition directions. Thus, the US array 40 is easy to fabricate.

The signal electrode terminals 52 are laid out in a straight line shape at every other US element on both end face sides of the US array 40. Therefore, a disposition spacing (pitch) P1 for the signal electrode terminals 52 on each end face side is twice a disposition pitch in a conventional US array in which the signal electrode terminals 52 are continuously laid out. The ground electrode terminals 51 are laid out in a straight line shape at every other US element on the left and on the right of the transmitting and receiving portions 60.

Note that the US array 40 is arranged in a three-dimensional curved surface shape. Strictly, the term "straight line shape" means "an arc shape" or that "arrangement at the time of projection onto a two-dimensional plane has a straight line shape."

Since the US unit 30 has the wider disposition pitch P1 for the signal electrode terminals 52, connection of the signal line 42 and the signal electrode terminal 52 is easy. Thus, the ultrasound unit 30 is easy to manufacture, and the ultrasound endoscope 2 having the US unit 30 is easy to manufacture.

Note that the plurality of signal lines 42 may be each one cable (wire) or the plurality of signal lines 42 may be disposed at a flexible wiring board. A connection method is, for example, solder joining. Since it is easy to enhance connection strength of a connection portion, the ultrasound unit 30 and the ultrasound endoscope 2 are high in reliability.

Since the plurality of ground electrode terminals 51 are laid out in a straight line shape, all the ground electrode terminals 51 can be connected by the two short-lines 41A and 41B. Each short-line 41 is only connected to the ground line 53 at at least one site.

The short-line 41 is made of a conductor in a line shape or a ribbon shape, such as aluminum or copper, and is connected to the ground electrode terminal 51 by a known method, such as ultrasound or heat. Alternatively, the short-line 41 may be formed by forming a conductive film made of a conductor, such as aluminum or copper, via, for example, a metal mask. The conductive film can be formed by sputtering, an evaporation method, or an electroplating method.

Since the plurality of ground electrode terminals 51 need not be connected to respective ground lines 53, the ultrasound unit 30 is easy to manufacture, and the ultrasound endoscope 2 having the ultrasound unit 30 is easy to manufacture.

Note that it is apparent that even if each ultrasound element has a transmitting and receiving portion in which piezoelectric layers of, e.g., PZT are stacked, instead of the transmitting and receiving portion 60, in which the plurality of capacitance type US cells 10 are laid out, the ultrasound element has same effects.

Second Embodiment

A US unit 30A according to a second embodiment and a US endoscope 2A having the US unit 30A will be described below. Since the US unit 30A and the US endoscope 2A are similar to the US unit 30 and the US endoscope 2, respectively, identical components are denoted by identical reference numerals, and a description of the components will be omitted.

Figure 10:
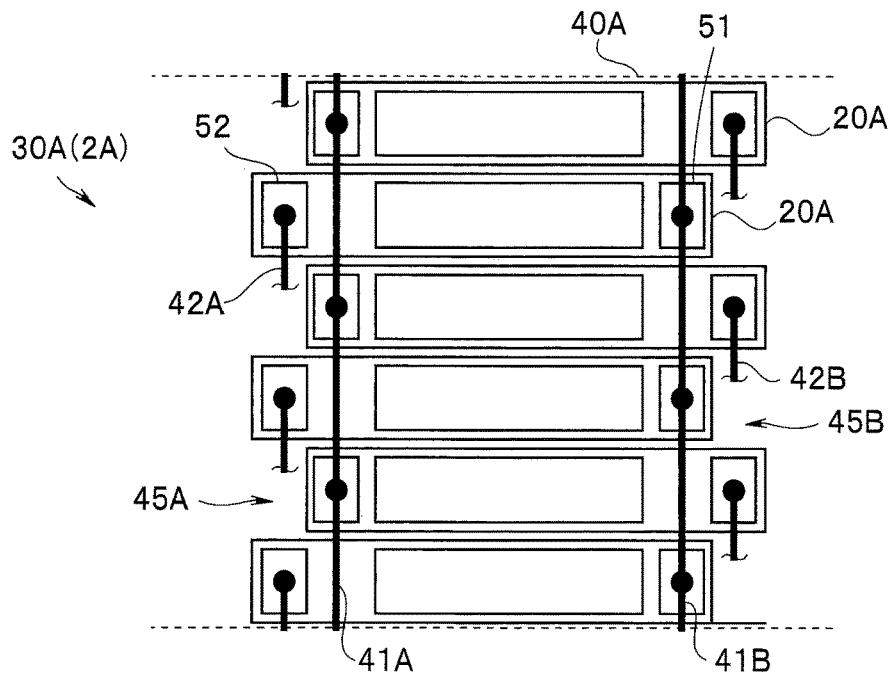
FIG. 10 is a plan developed view of an ultrasound array of an ultrasound unit according to a second embodiment.

As shown in FIG. 10, in a US array 40A of the US unit 30A, a plurality of ultrasound elements 20A are coupled such that shorter sides of the ultrasound elements 20A are positioned in a zigzag manner at both end faces of the ultrasound array 40A. Therefore, notch portions 45A and 45B are formed at the both end faces of the ultrasound array 40A. A signal line 42 is provided to extend to a second principal surface 20SB side, i.e., an inner portion side of the ultrasound array 40A in a hollow cylinder shape via the notch portion 45.

The US unit 30A has the same effects as the US unit 30. Additionally, the signal lines 42 do not protrude from the both end faces of the ultrasound array 40A. Thus, a dimension of a longer side of the US element 20A is shorter in the US unit 30A. The US endoscope 2A including the US unit 30A has a shorter distal end portion 37.

In addition, the US unit 30A can reduce interference between the adjacent signal lines 42. That is, in the US unit 30 shown in FIG. 8, the signal lines 42A and 42B are led out in parallel with a longitudinal direction of the US element 20. Therefore, the signal lines 42A and 42B become arched, and deflection or the like occurs. If the amount of deflection of the adjoining signal lines 42A and 42B is large, the signal lines 42A and 42B may interfere with one another.

In contrast, in the US unit 30A shown in FIG. 10, the signal lines 42A and 42B are each passed through the notch 45A or 45B that is an empty space at a predetermined site, and thus the signal lines 42A and 42B are in no danger of interfering with one another.

Third Embodiment

A US unit 30B according to a third embodiment and a US endoscope 2B having the US unit 30B will be described below. Since the US unit 30B and the US endoscope 2B are similar to the US unit 30 and the US endoscope 2, respectively, identical components are denoted by identical reference numerals, and a description of the components will be omitted.

Figure 11:
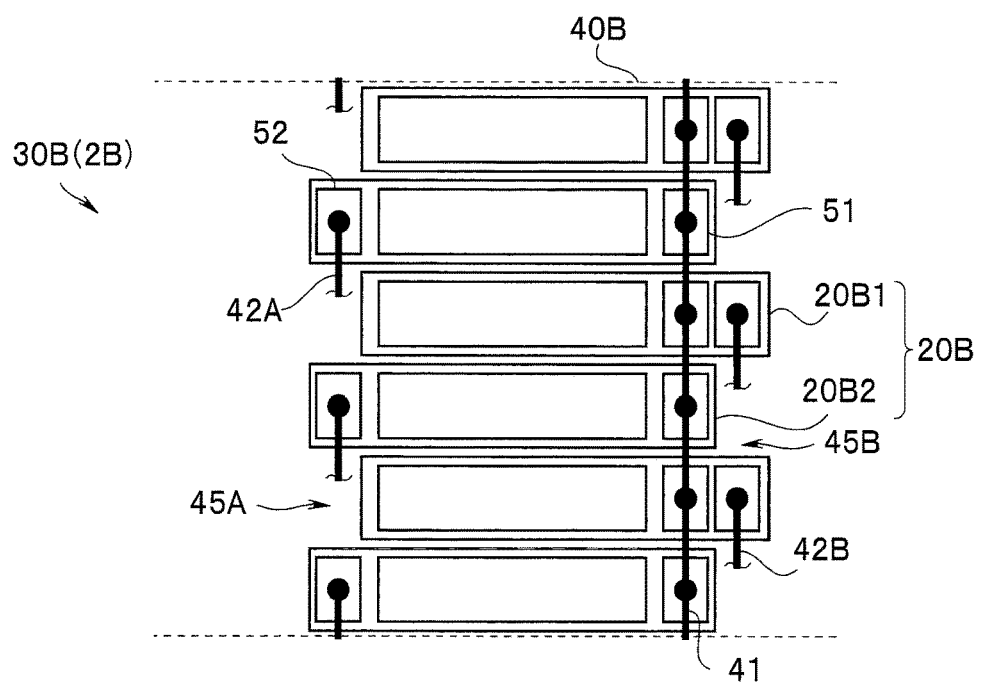
FIG. 11 is a plan developed view of an ultrasound array of an ultrasound unit according to a third embodiment.

As shown in FIG. 11, there are two types of ultrasound elements 20B constituting a US array 40B of the US unit 30B. That is, the ultrasound element 20B is either a first ultrasound element 20B1 or a second ultrasound element 20B2. In the first ultrasound element 20B1, a ground electrode terminal 51 is arranged between a signal electrode terminal 52 and a transmitting and receiving portion 60 at a first principal surface 20SA. In the second ultrasound element 20B2, the transmitting and receiving portion 60 is arranged between the ground electrode terminal 51 and the signal electrode terminal 52 at the first principal surface 20SA. The first ultrasound element 20B1 and the second ultrasound element 20B2 are coupled such that the ground electrode terminals 51 adjoin each other.

Additionally, since the two different ultrasound elements 20B1 and 20B2 are coupled such that shorter sides are positioned in a zigzag manner, a plurality of notch portions 45A and 45B are formed at both end faces of the US array 40B. A signal line 42 is provided to extend to a second principal surface 20SB side via the notch portion 45.

As shown in FIG. 11, one short-line 41 is enough in the US unit 30B. Thus, a dimension in a longer side direction of the US element 20B is shorter than the US element 20.

The US unit 30B has effects which the US unit 30 and the like have and is even shorter. The US endoscope 2B has effects which the US endoscope 2 has and has an even shorter distal end portion 37.

As has been described above, an ultrasound unit according to the embodiment may have the configuration below.

An ultrasound unit wherein the plurality of ultrasound elements are made up of a plurality of first ultrasound elements, in each of which the ground electrode terminal is arranged between the signal electrode terminal and the transmitting and receiving portion, and a plurality of second ultrasound elements, in each of which the transmitting and receiving portion is arranged between the ground electrode terminal and the signal electrode terminal, and the first ultrasound elements and the second ultrasound elements are coupled such that the ground electrode terminals adjoin one another.

Fourth Embodiment

A US unit 30C according to a fourth embodiment and a US endoscope 2C having the US unit 30C will be described below. Since the US unit 30C and the US endoscope 2C are similar to the US unit 30 and the US endoscope 2, respectively, identical components are denoted by identical reference numerals, and a description of the components will be omitted.

Figure 12:
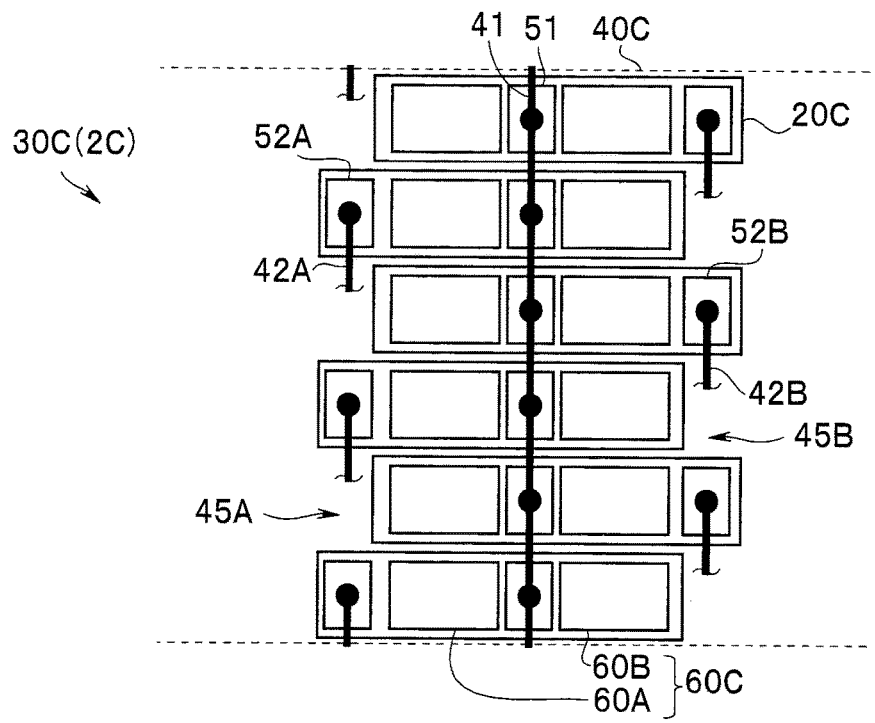
FIG. 12 is a plan developed view of an ultrasound array of an ultrasound unit according to a fourth embodiment.

As shown in FIG. 12, in a US element 20C of the US unit 30C, a signal electrode terminal 52 is arranged at one end portion, and a ground electrode terminal 51 is arranged at a center of a transmitting and receiving portion 60C which is divided into two, a first transmitting and receiving portion 60A and a second transmitting and receiving portion 60B.

A signal line (a piece of signal wiring) 42 is provided to extend to a second principal surface 20SB side via a notch portion 45 at an end portion. A plurality of ground electrode terminals 51 are connected by one short-line 41. Note that a ground line (not shown) connected to the short-line 41 is led out via a coupling portion (between the adjoining transmitting and receiving portions 60C) of the adjoining US elements 20C or is led out via a piece of through-wiring.

The US unit 30C and the US endoscope 2C have effects which the US unit 30B and the like have.

Fifth Embodiment

A US unit 30D according to a fifth embodiment and a US endoscope 2D having the US unit 30D will be described below. Since the US unit 30D and the US endoscope 2D are similar to the US unit 30 and the US endoscope 2, respectively, identical components are denoted by identical reference numerals, and a description of the components will be omitted.

Figure 13:
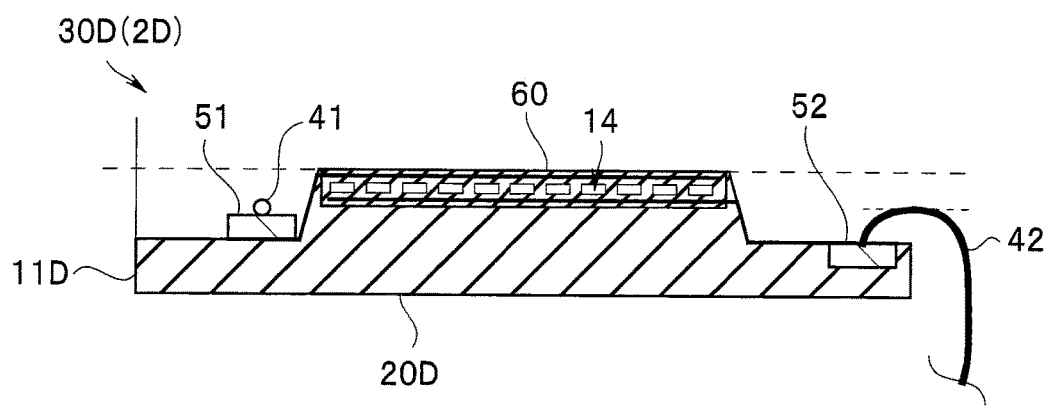
FIG. 13 is a cross-sectional view of an ultrasound element of an ultrasound unit according to a fifth embodiment.

As shown in FIG. 13, in a US element 20D of the US unit 30D, a surface where a signal electrode terminal 52 is disposed and a surface where a ground electrode terminal 51 is disposed are lower than a surface of a transmitting and receiving portion 60. A height of the surface of the transmitting and receiving portion 60 is higher than a maximum height of a signal line 42 and a maximum height of a ground line 53 (not shown). That is, a silicon substrate 11D as a base is stepped at end portions such that, even if the signal line 42 is connected to the signal electrode terminal 52, a short-line 41 and the ground line 53 are connected to the ground electrode terminal 51, the height of each of the components does not exceed the height of the transmitting and receiving portion 60.

The US unit 30D and the US endoscope 2D have effects which the US unit 30 and the like have. Additionally, in the US unit 30D with a plurality of US elements 20D disposed in a hollow cylindrical shape, a piece of wiring (wire) and the like do not protrude beyond the surface of the transmitting and receiving portion 60. Thus, the US unit 30D and a distal end portion 37 of the US endoscope 2D have smaller outer diameters.

Sixth Embodiment

A US unit 30E according to a sixth embodiment and a US endoscope 2E having the US unit 30E will be described below. Since the US unit 30E and the US endoscope 2E are similar to the US unit 30 and the US endoscope 2, respectively, identical components are denoted by identical reference numerals, and a description of the components will be omitted.

Figure 14:
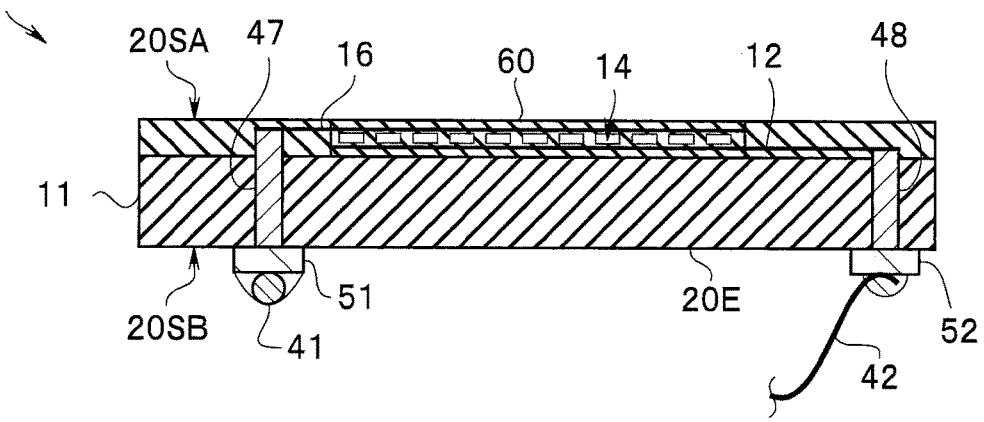
FIG. 14 is a cross-sectional view of an ultrasound element of an ultrasound unit according to a sixth embodiment.

As shown in FIG. 14, in a US element 20E of the US unit 30E, a transmitting and receiving portion 60 is disposed at a first principal surface 20SA, and a ground electrode terminal 51 and a signal electrode terminal 52 are disposed at a second principal surface 20SB. The ground electrode terminal 51 and an upper electrode 16 are connected via a piece 47 of through-wiring which pierces through a silicon substrate 11 as a base, and the signal electrode terminal 52 and a lower electrode 12 are connected via a piece 48 of through-wiring.

That is, in the US element 20E, the transmitting and receiving portion 60 is formed at the first principal surface 20SA of the base having the first principal surface 20SA and the second principal surface 20SB, and the signal electrode terminal 52 and the ground electrode terminal 51 are formed at the second principal surface 20SB. Note that a piece of wiring may be provided to extend to the second principal surface 20SB of the silicon substrate 11 by using a different wiring method, such as pieces of side face wiring, instead of the pieces 47 and 48 of through-wiring.

Figure 15:
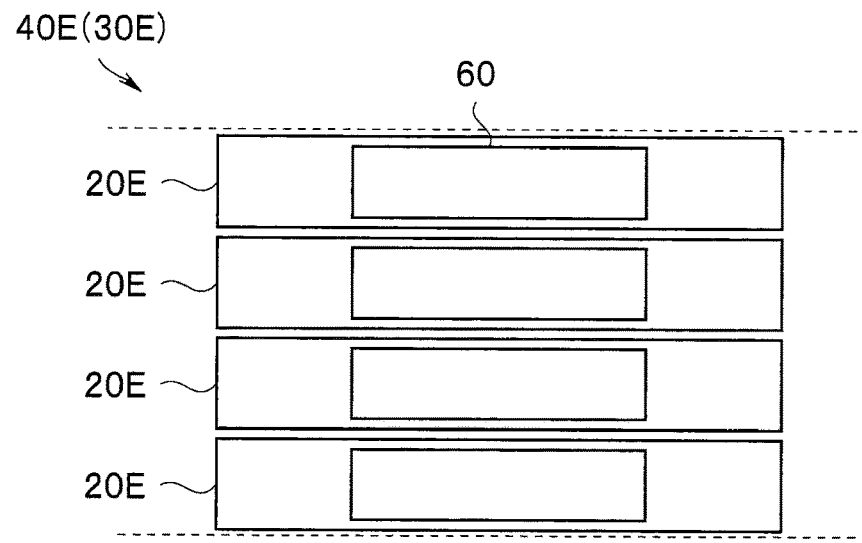
FIG. 15 is a top view of an ultrasound array of the ultrasound unit according to the sixth embodiment.
Figure 16:
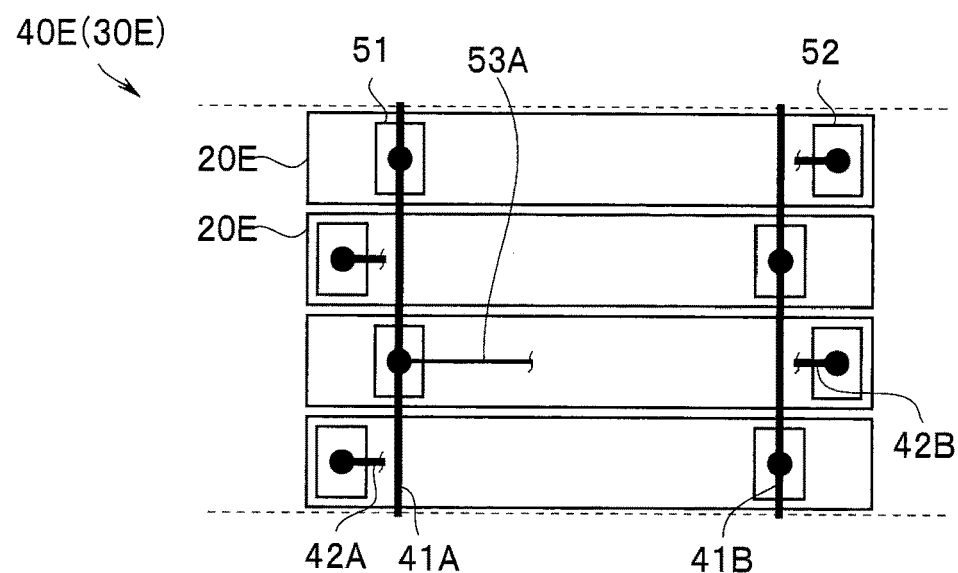
FIG. 16 is a bottom view of the ultrasound array of the ultrasound unit according to the sixth embodiment.

As shown in FIGS. 15 and 16, in a US array 40E, the transmitting and receiving portion 60 is arranged substantially at a center of the first principal surface 20SA. The signal electrode terminals 52 disposed at the second principal surfaces 20SB are laid out alternately at end portions on opposite sides of the transmitting and receiving portions 60 disposed at the first principal surfaces 20SA to have a straight line shape. A plurality of ground electrode terminals 51 are laid out in a straight line shape in two rows closer to a center than the signal electrode terminals 52.

As in the US array 40 shown in FIG. 8, a plurality of signal lines 42 are each connected to the signal electrode terminal 52 of one US element 20E. Two short-lines 41 each connect the ground electrode terminals 51 of a plurality of US elements 20E and are each connected to a corresponding ground line 53 at one site.

Note that the signal lines 42 and the ground lines 53 are provided to extend to an inner side of the US array 40E so as not to protrude from end faces of the US array 40E.

The US unit 30E and the US endoscope 2E have effects which the US unit 30 and the like have and have even smaller outer diameters.

Modifications of Sixth Embodiment

US units 30F and 30G according to a modification 1 and a modification 2 of the sixth embodiment and US endoscopes 2F and 2G having the US units 30F and 30G will be described below. Since the US units 30F and 30G and the US endoscopes 2F and 2G are similar to the US unit 30E and the US endoscope 2E, respectively, identical components are denoted by identical reference numerals, and a description of the components will be omitted.

Figure 17:
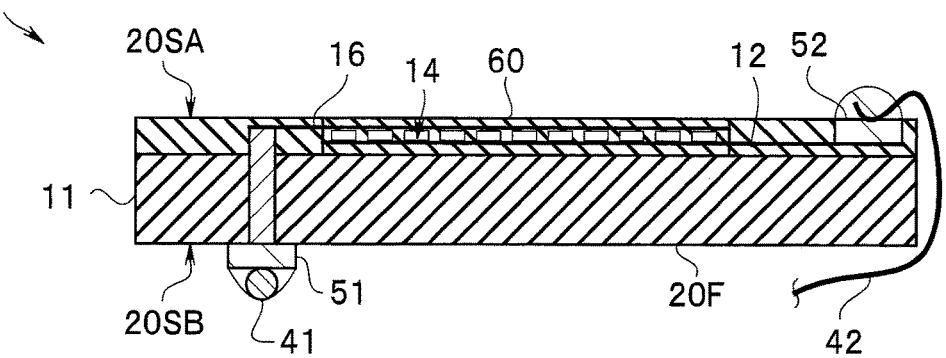
FIG. 17 is a cross-sectional view of an ultrasound element of an ultrasound unit according to a modification 1 of the sixth embodiment.

As shown in FIG. 17, in a US element 20F of the US unit 30F, a transmitting and receiving portion 60 and a signal electrode terminal 52 are disposed at a first principal surface 20SA, and a ground electrode terminal 51 is disposed at a second principal surface 20SB.

A plurality of US elements 20F are coupled in a state where the US elements 20F are alternately rotated by 180° along a longer side direction. Therefore, the signal electrode terminals 52 connected to signal lines 42 are arranged alternately at end portions on the first principal surface 20SA side. The ground electrode terminals 51 connected to short-lines 41 are arranged alternately at both end portions on the second principal surface 20SB side to have a straight line shape.

The US unit 30F and the US endoscope 2F have effects which the US unit 30E and the like have and are even shorter.

Figure 18:
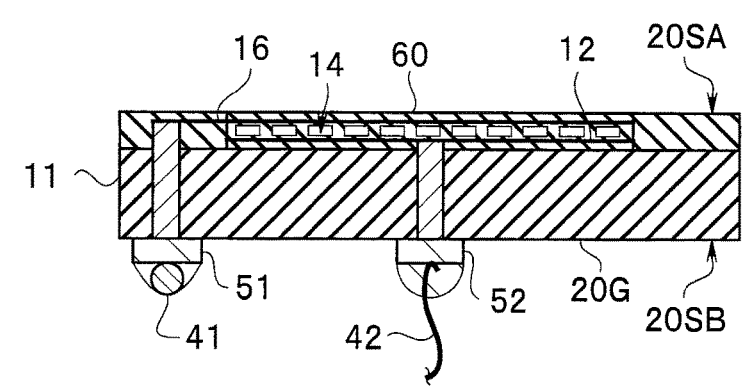
FIG. 18 is a cross-sectional view of an ultrasound element of an ultrasound unit according to a modification 2 of the sixth embodiment.

As shown in FIG. 18, in a US element 20G of the US unit 30G, a transmitting and receiving portion 60 is disposed substantially at a center portion of a first principal surface 20SA, and a ground electrode terminal 51 and a signal electrode terminal 52 are disposed at a second principal surface 20SB. The signal electrode terminal 52 here is disposed substantially at a center portion of the second principal surface 20SB.

A plurality of US elements 20G are coupled in a state where the US elements 20G are alternately rotated by 180° along a longer side direction. Therefore, the ground electrode terminals 51 connected to a short line 41 are arranged alternately at end portions on the second principal surface 20SB side. The signal electrode terminals 52 connected to signal lines 42 are arranged in a straight line shape at a center portion on the second principal surface 20SB side. Thus, all the ground electrode terminals 51 can be connected by the one short-line 41.

The US unit 30G and the US endoscope 2G have effects which the US unit 30E and the like have and are even shorter.

As has been described above, at least one of a signal electrode terminal and a ground electrode terminal and a transmitting and receiving portion may be disposed at a first principal surface of an ultrasound element.

The present invention is not limited to the above-described embodiments or modifications. Various changes, alterations, and the like can be made without departing from spirit of the present invention.

What is claimed is:

1. An ultrasound unit comprising:
   an ultrasound array having a plurality of separated ultrasound elements, each of the plurality of ultrasound elements comprising:
   a rectangular substrate having a pair of short sides and a pair of long sides, the long sides being longer than the short sides;
   a transmitting and receiving portion disposed on a surface of the substrate for transmitting and receiving ultrasound;
   a ground electrode and a ground electrode terminal connected to the ground electrode, the ground electrode terminal being disposed on the surface of the substrate adjacent to one of the pair of short sides; and
   a signal electrode and a signal electrode terminal connected to the signal electrode, the signal electrode terminal being disposed on the surface of the substrate adjacent to an other one of the pair of short sides;
   one or more common lines that are connected to the ground electrode terminal for each of the plurality of ultrasound elements;
   a ground line that is connected to each of the one or more common lines; and
   a signal line connected to each of the signal electrode terminals,
   wherein the plurality of ultrasound elements are coupled together along adjacent long sides such that adjoining first and second ultrasound elements of the plurality of ultrasound elements are configured such that:
   the first ultrasound element having the ground electrode terminal disposed adjacent to a first short side of the pair of short sides and having the signal electrode terminal disposed adjacent to a second short side of the pair of short sides opposite to the first short side;
   the second ultrasound element having the signal electrode terminal disposed adjacent to the first short side and the ground electrode terminal disposed adjacent to the second short side; and
   the first short side of the first ultrasound element is adjacent the second short side of the second ultrasound element and the second short side of the first ultrasound element is adjacent the first short side of the second ultrasound element.

2. The ultrasound unit according to claim 1, wherein the one or more common lines are laid out in a straight line shape when viewed in a radial direction.

3. The ultrasound unit according to claim 2, wherein the plurality of ultrasound elements, when coupled together along the adjacent long sides, form a cylindrical shape.

4. The ultrasound unit according to claim 3, wherein at least one of the signal electrode terminal and the ground electrode terminal, and the transmitting and receiving portion are disposed at a first principal surface of each of the plurality of ultrasound elements.

5. The ultrasound unit according to claim 4, wherein the transmitting and receiving portion, the signal electrode terminal, and the ground electrode terminal are disposed at the first principal surface of each of the plurality of ultrasound elements.

6. The ultrasound unit according to claim 5, wherein a first set of the plurality of ultrasound elements identical in a form in which the transmitting and receiving portion, the signal electrode terminal, and the ground electrode terminal are arranged are coupled in a state where the ultrasound elements are alternately rotated by 180° along a long side direction as compared to a second set of the plurality of ultrasound elements.

7. The ultrasound unit according to claim 6, wherein a plurality of ultrasound cells are disposed at the transmitting and receiving portion, each of the plurality of ultrasound cells has a signal electrode portion and a ground electrode portion that are arranged to face each other across a cavity, a plurality of the signal electrode portions comprise the signal electrode, and a plurality of the ground electrode portions comprise the ground electrode.

8. The ultrasound unit according to claim 5, wherein
   the plurality of ultrasound elements are coupled together such that the short sides are positioned in a zigzag manner at either end face of the ultrasound array to form a plurality of notch portions, and
   the signal line is provided to extend to a second principal surface side via the notch portion.

9. The ultrasound unit according to claim 5, wherein a height of a surface of the transmitting and receiving portion is higher than a maximum height of the signal line and a maximum height of the ground line.

10. The ultrasound unit according to claim 9, wherein a first set of the plurality of ultrasound elements identical in a form in which the transmitting and receiving portion, the signal electrode terminal, and the ground electrode terminal are arranged are coupled in a state where the ultrasound elements are alternately rotated by 180° along a long side direction as compared to a second set of the plurality of ultrasound elements.

11. The ultrasound unit according to claim 10, wherein a plurality of ultrasound cells are disposed at the transmitting and receiving portion, the signal electrode terminal and the ground electrode terminal for the adjoining first and second ultrasound elements are arranged to oppose each other across a cavity, a plurality of the signal electrode portions comprise the signal electrode, and a plurality of the ground electrode portions comprise the ground electrode.

* * * * *